United States Patent
Shen et al.

(10) Patent No.: US 12,075,723 B2
(45) Date of Patent: Sep. 3, 2024

(54) ADAPTIVE DEVICE FOR HEADER CAPABLE OF PERFORMING LODGING DETECTION BASED ON LASER SENSOR AND CONTROL METHOD THEREOF

(71) Applicant: JIANGSU UNIVERSITY, Zhenjiang (CN)

(72) Inventors: Yue Shen, Zhenjiang (CN); Lingfei Zhang, Zhenjiang (CN); Jinming Chen, Zhenjiang (CN); Wei Du, Zhenjiang (CN); Zhipeng Du, Zhenjiang (CN)

(73) Assignee: JIANGSU UNIVERSITY, Zhenjiang (CN)

( * ) Notice: Subject to any disclaimer, the term of this patent is extended or adjusted under 35 U.S.C. 154(b) by 0 days.

(21) Appl. No.: 17/927,901

(22) PCT Filed: Feb. 15, 2022

(86) PCT No.: PCT/CN2022/076341
§ 371 (c)(1),
(2) Date: Nov. 28, 2022

(87) PCT Pub. No.: WO2023/019892
PCT Pub. Date: Feb. 23, 2023

(65) Prior Publication Data
US 2024/0224858 A1    Jul. 11, 2024

(30) Foreign Application Priority Data
Aug. 16, 2021    (CN) .......................... 202110941342.3

(51) Int. Cl.
*A01D 41/12*    (2006.01)
*A01D 41/127*    (2006.01)
(Continued)

(52) U.S. Cl.
CPC .......... *A01D 41/1274* (2013.01); *G01S 17/88* (2013.01); *G05B 11/42* (2013.01)

(58) Field of Classification Search
CPC ...... A01D 41/1274; G01S 17/88; G05B 11/42
See application file for complete search history.

(56) References Cited

U.S. PATENT DOCUMENTS 8,474,306 B1 * 7/2013 Behroozi ............... G01N 13/02
                                                             73/64.52
11,908,074 B2 * 2/2024 Kiss ..................... G01C 11/025
(Continued)

FOREIGN PATENT DOCUMENTS

CN    106508256 A    3/2017
CN    108260401 A    7/2018
(Continued)

*Primary Examiner* — Tyler J Lee
(74) *Attorney, Agent, or Firm* — Bayramoglu Law Offices LLC

(57) ABSTRACT

An adaptive device includes an transmission assembly and a laser sensor control assembly, where the transmission assembly includes a rotating shaft of a roller, a harvesting part, a motor base plate, a transmission belt of the harvesting part, a transmission shaft of a motor A, motor arms, the high-power motor A, a high-power motor B, a transmission shaft of the motor B, a transmission belt of the roller, and a rotating shaft of the harvesting part; and the laser sensor control assembly includes the motor base plate, upright lifting columns, a control base plate, a battery, a power distribution board, a voltage reduction module, electronic speed controllers, a main control board, a low-power motor, a laser sensor base plate, a laser sensor, tube clamps, a rotating shaft of the laser sensor, and a bearing for stabilizing the rotating shaft of the laser sensor.

8 Claims, 2 Drawing Sheets

(51) Int. Cl.
*G01S 17/88* (2006.01)
*G05B 11/42* (2006.01)

(56) References Cited

U.S. PATENT DOCUMENTS

| | | | | |
|---|---|---|---|---|
| 11,987,120 | B2* | 5/2024 | Muench | A01D 69/03 |
| 2013/0223189 | A1* | 8/2013 | Davis, III | G01C 15/00 |
| | | | | 367/99 |
| 2014/0163781 | A1* | 6/2014 | Vian | G01S 7/4802 |
| | | | | 701/3 |
| 2017/0016870 | A1* | 1/2017 | McPeek | A01D 41/127 |
| 2017/0082442 | A1* | 3/2017 | Anderson | A01B 69/007 |
| 2017/0334560 | A1* | 11/2017 | O'Connor | G05D 1/104 |
| 2019/0220964 | A1* | 7/2019 | Mello | A01B 79/005 |
| 2019/0274257 | A1* | 9/2019 | Papanikolopoulos | G06T 17/10 |
| 2021/0327132 | A1* | 10/2021 | Kiss | G06Q 50/02 |
| 2023/0309446 | A1* | 10/2023 | Wigdahl | A01D 41/1274 |
| | | | | 56/10.2 R |
| 2023/0320274 | A1* | 10/2023 | Vandike | A01B 79/005 |
| | | | | 701/50 |

FOREIGN PATENT DOCUMENTS

| | | | |
|---|---|---|---|
| CN | 109068591 | A | 12/2018 |
| CN | 109275411 | A | 1/2019 |
| CN | 112888304 | A | 6/2021 |
| CN | 113661827 | A | 11/2021 |
| DE | 3627015 | A1 | 2/1988 |

\* cited by examiner

1

ADAPTIVE DEVICE FOR HEADER CAPABLE OF PERFORMING LODGING DETECTION BASED ON LASER SENSOR AND CONTROL METHOD THEREOF

CROSS REFERENCE TO THE RELATED APPLICATIONS

This application is the national phase entry of International Application No. PCT/CN2022/076341, filed on Feb. 15, 2022, which is based upon and claims priority to Chinese Patent Application No. 202110941342.3, filed on Aug. 16, 2021, the entire contents of which are incorporated herein by reference.

TECHNICAL FIELD

The present disclosure relates to the technical field of agricultural machinery, and in particular, relates to an adaptive device for a header capable of performing lodging detection based on a laser sensor and a control method thereof.

BACKGROUND

In the lodging state of crops, when combine harvesters perform harvesting in an ordinary way, some crops to be harvested may not be harvested, resulting in a great deal of waste. In order to solve this problem, the traditional combine harvester typically lowers a harvesting part by means of a control terminal to maximally ensure that all the crops are harvested. However, this method has low accuracy because the state of the crops is completely determined by human eyes and the experience of operators. Besides, the method is quite time-consuming and energy-consuming. In the current social background of labor shortage, it is necessary to provide a combine harvester capable of automatically identifying the lodging state and controlling the harvesting.

Chinese patent CN109068591 discloses a combine harvester which is controlled to move at an appropriate speed according to its loss amount calculated by means of a sensor. In this way, the loss can be reduced to a certain extent. Nevertheless, the problem of harvesting of the crops in the lodging state is not fundamentally solved. The operating accuracy is quite low. Moreover, when the crops in the lodging state are extremely concentrated in an area, a very small quantity of crops can be harvested, resulting in a control failure.

The design of the traditional combine harvester focuses on its internal structure to reduce the internal loss of the traditional combine harvester. However, during actual harvesting, the loss generated due to low harvesting accuracy caused by the lodging of the crops is considerably greater than the internal loss. Through improvement of the internal structure of the traditional combine harvester, the loss is reduced to a certain extent, but optimization is not performed to solve the root cause of the loss.

A combine harvester disclosed in patent CN112888304 can process crops for multiple times. In spite of this, the crops are merely processed in the combine harvester, and the problem of harvesting of the crops in the lodging state is still not solved.

At present, an intelligent combine harvester capable of solving the problem of harvesting of the crops in the lodging state is not developed in domestic. When facing the crops in the lodging state, the combine harvesters are adjusted manually in most cases for operation, resulting in low accuracy, time consumption, and labor consumption. Compared with the harvesting part of the traditional combine harvester, the present disclosure has lower costs and higher reliability. The present disclosure can intelligently determine the state of the crops, and adopts machine identification instead of human identification, thus improving the operating accuracy and saving the labor and time.

SUMMARY

The objective of the present disclosure is to provide an adaptive device for a header capable of performing lodging detection based on a laser sensor and a control method thereof. The adaptive device has high operability, a low cost, outstanding reliability, a simple structure, and strong adaptability. The adaptive device determines the state of crops by means of a laser sensor to control crop harvesting accuracy of the harvesting part of a combine harvester in advance, thus being adapted to fine operation. The structural feature of the adaptive device is that a scanning position of the laser sensor is adjusted by means of a low-power motor, such that the laser sensor scans up and down within a constant angle at a preset speed, so as to obtain three-dimensional point cloud data of crops in front of the harvesting part. Accordingly, the state of the crops can be determined.

The present disclosure adopts the following technical solution. The adaptive device for the header capable of performing lodging detection based on the laser sensor includes a transmission assembly and a laser sensor control assembly, where the transmission assembly includes a rotating shaft (1) of a roller, a harvesting part (2), a motor base plate (4), a transmission belt (5) of the harvesting part, a transmission shaft (6) of a motor A, motor arms (7), the high-power motor A (8), a high-power motor B (10), a transmission shaft (11) of the motor B, a transmission belt (12) of the roller, and a rotating shaft (14) of the harvesting part; the motor base plate (4) is fixed to an upper end of the harvesting part (2); the high-power motor A (8) and the high-power motor B (10) are symmetrically fixed to the motor base plate (4) via positioning holes; the high-power motor A (8) is connected to the transmission shaft (6) of the motor A via a positioning hole in the corresponding motor arm (7), and the transmission shaft (6) of the motor A transmits torque to the rotating shaft (14) of the harvesting part through the transmission belt (5) of the harvesting part for transmission; and the high-power motor B (10) is connected to the transmission shaft (11) of the motor B via a positioning hole in the corresponding motor arm (7), and the transmission shaft (11) of the motor B transmits torque to the rotating shaft (1) of the roller through the transmission belt (12) of the roller for transmission; and the laser sensor control assembly includes the motor base plate (4), upright lifting columns (13), a control base plate (15), a battery (16), a power distribution board (17), a voltage reduction module (18), electronic speed controllers (19), a main control board (20), a low-power motor (21), a laser sensor base plate (22), a laser sensor (23), tube clamps (24), a rotating shaft (25) of the laser sensor, and a bearing (26) for stabilizing the rotating shaft of the laser sensor; the control base plate (15) is arranged above the motor base plate (4) through the upright lifting columns (13); the battery (16), the power distribution board (17), the voltage reduction module (18), the main control board (20), and three electronic speed controllers (19) are all bonded to the control base plate (15) with double-sided adhesives; the low-power motor (21) is fixed to the control base plate (15) through an L-shaped support and close to a front end of the control base plate (15); one end of the rotating shaft (25) of the laser sensor is connected to the low-power motor (21) through the motor arm (7), and the other end of the rotating shaft (25) of the laser sensor is fixed by the bearing (26) for stabilizing the rotating shaft of the laser sensor; and the laser sensor (23) is fixed at the center of the rotating shaft (25) of the laser sensor through the laser sensor base plate (22) by means of the tube clamps (24).

Further, the battery (16), the power distribution board (17), the voltage reduction module (18), the main control board (20), and the low-power motor (21) are fixed above the control base plate (15); the high-power motor A (8) and the high-power motor B (10) are symmetrically fixed below the control base plate (15); a positive electrode and a negative electrode of the battery are connected to the power distribution board through wires; the power distribution board leads wires to the three electronic speed controllers (19); the electronic speed controllers convert a direct current into a three-phase current, and are respectively connected to the high-power motor A, the high-power motor B, and the low-power motor through wires, so as to control rotation of the rotating shaft; the power distribution board also leads a wire to the voltage reduction module and then to a power interface of the main control board; and a pulse-width modulation (PWM) channel of the main control board is connected to a PWM signal wire of the electronic speed controller, so as to achieve a control over the motor.

Further, four power wires are led from the battery (16); two of the power wires are connected to the power distribution board to shunt a heavy current of the motor; and the other two of the power wires are connected to the voltage reduction module to provide an input voltage for the voltage reduction module.

Further, the voltage reduction module (18) is used to reduce the input voltage and limit the current, an input terminal of the voltage reduction module (18) is connected to the main control board through two 14 awg silicone wires; the power distribution board receives a voltage from a power supply terminal, and four power output wires from the power distribution board are connected to two electronic speed controllers; the electronic speed controller is connected to two power input wires from the power distribution board, and is also connected to one signal input wire and one analog signal ground wire from the main control board; and three output wires from the electronic speed controller is connected to the motor.

A control method of an adaptive device for a header capable of performing lodging detection based on a laser sensor includes the following steps:

step 1, turning on a main switch of a power supply to make a low-power motor (21) and a main control board (20) be respectively powered on, where a high-power motor A (8) and a high-power motor B (10) are powered on through an internal diesel generator;

step 2, when a combine harvester moves forwards, controlling, by the main control board (20), the high-power motor A (8) to adjust a harvesting part to be horizontal, and presetting, through the main control board (20), a basic rotation speed for the high-power motor B (10);

step 3, performing data preprocessing on a laser sensor (23) through the following steps: firstly, extracting, based on a region of interest (ROI), data only retained within a threshold range of a preset region in front of the combine harvester; and secondly, filtering outliers in the data by means of a statistical filter;

step 4, presetting a basic rotation speed for the low-power motor (21) such that the low-power motor (21) drives the laser sensor (23) to repeatedly scan up and down within a constant angle;

and receiving and storing, by a microprocessor, point cloud data of the laser sensor, and displaying, by the microprocessor, the point cloud data within a complete scanning cycle on a serial screen; and step 5, analyzing and preprocessing, by the microprocessor, the laser point cloud data of N frames, and adjusting, by the microprocessor, an output according to a proportion integration differentiation (PID) to select different harvesting modes.

Further, the scanning of the laser sensor is mainly fulfilled based on a time-of-flight (TOF) principle.

Further, the step 4 specifically includes:

obtaining, based on a scanning frequency of the laser sensor, the time $t_{laser}$ required for acquiring the data of one frame by the laser sensor, and calculating the time $t_{cycle}$ of a complete up-down scanning cycle according to the basic rotation speed n and magnitude θ of the constant angle of the low-power motor, so that the number N of frames of the laser sensor within the constant angle can be calculated:

$$\omega = 2\pi n \qquad (1)$$

$$t_{cycle} = \frac{\theta}{\omega} \qquad (2)$$

$$N = \text{int}\left(\frac{t_{cycle}}{t_{laser}}\right) \qquad (3)$$

where, ω represents an angular speed of the low-power motor; int( ) indicates rounding of the number of the frames of the laser sensor; N represents the number of laser frames, worked out according to formula (1), formula (2), and formula (3), within a complete up-down scanning angle; and the microprocessor receives and stores the laser point cloud data of N frames, and displays the laser point cloud data on the serial screen, such that distance information of an object in front of the combine harvester can be visually observed.

Further, the step 5 specifically includes:

receiving and storing, by the microprocessor, the laser point cloud data of N frames, and processing, by the microprocessor, the data of N frames, which is taken as being within the complete scanning cycle, through the following steps: firstly, solving a ground fitting equation (4) by means of a least square method to obtain values of parameter a, parameter b, parameter c, and parameter d:

$$ax+by+cy=d \qquad (4)$$

working out a planar thresh $d_i$ of any data point $(x_i,y_i,z_i)$; setting the planar thresh as Δd, where if $|d_i-d|<\Delta d$ the point is regarded as a ground point; and filtering the ground point;

secondly, performing density-based spatial clustering of applications with noise (DBSCAN) on non-ground point cloud data, so as to cluster the data of the object into different clusters by region growing; analyzing features of each cluster according to a clustering result, where the data distribution of crops in a lodging state is obviously different from that of crops in a normal growth state:

an amount of point cloud data of the crops in the lodging state is generally small in a vertical direction; the crops in the lodging state tilt and extend towards a horizontal direction and are intertwined, so that an amount of the point cloud data of the crops in the lodging state is large in the horizontal direction; point cloud data of crops in a normal growth state is evenly distributed in the vertical direction, and an amount of the point cloud data of the crops in the normal growth state is large in the vertical direction; besides, the crops in the normal growth state are uniformly spaced in the horizontal direction, and an obvious jump of the data points in the horizontal direction exists; in this case, the state of the crops can be distinguished according to feature information, based on the clustering result, of the data; if a detection result shows that the crops are in the lodging state, the combine harvester slows down and lowers the harvesting part to guarantee harvesting accuracy, and restores an original speed and enables the harvesting part to return to be horizontal after the crops in a lodging area are completely harvested; and if the detection result shows that the crops are not in the lodging state, the combine harvester continues to move at the original speed and keeps the harvesting part horizontal to guarantee a harvesting speed.

The present disclosure has the following beneficial effects:

(1) The state of the crops is detected by means of the laser sensor, and the harvesting part is selectively lowered, so that the harvesting accuracy is improved, and the loss in the process of harvesting the crops once more is reduced. Accordingly, economic benefits are increased.

(2) The low-power motor operates at the preset basic rotation speed to drive the laser sensor to repeatedly scan up and down within the constant angle, so that a function that a two-dimensional laser sensor acquires data information of a three-dimensional space is fulfilled. Accordingly, the cost is low, and the resolution of the data is increased.

(3) A detection range of the laser sensor is divided, and ground point cloud data is filtered, so that the amount of the point cloud data is effectively decreased. Accordingly, the real-time capability of an algorithm and accuracy of detection on the crops are improved.

(4) The clusters in any shape in a data space can be found by means of the DBSCAN, and has a certain anti-noise capability. The features of the cluster are analyzed and extracted based on the clustering result, so that the state of the crops can be accurately obtained.

(5) During harvesting, the speed of the combine harvester is adjusted according to the state of the crops. When it is detected that the crops are in the lodging state, the combine harvester appropriately slows down; and when it is detected that the crops are not in the lodging state, the combine harvester continues to move at the original speed. By adjusting the speed of the combine harvester according to the state of the crops, operational efficiency of the combine harvester is enhanced.

(6) The scanning angle of the laser sensor is controlled by the low-power motor to be adapted to the lodging detection on different crops, so that a possible omission, caused by a manual adjustment on lowering of the harvesting part, of the crops in the lodging state is decreased, the degree of intelligence of the whole adaptive device is improved, and an operating process based on a human judgment is omitted.

Figure 1:
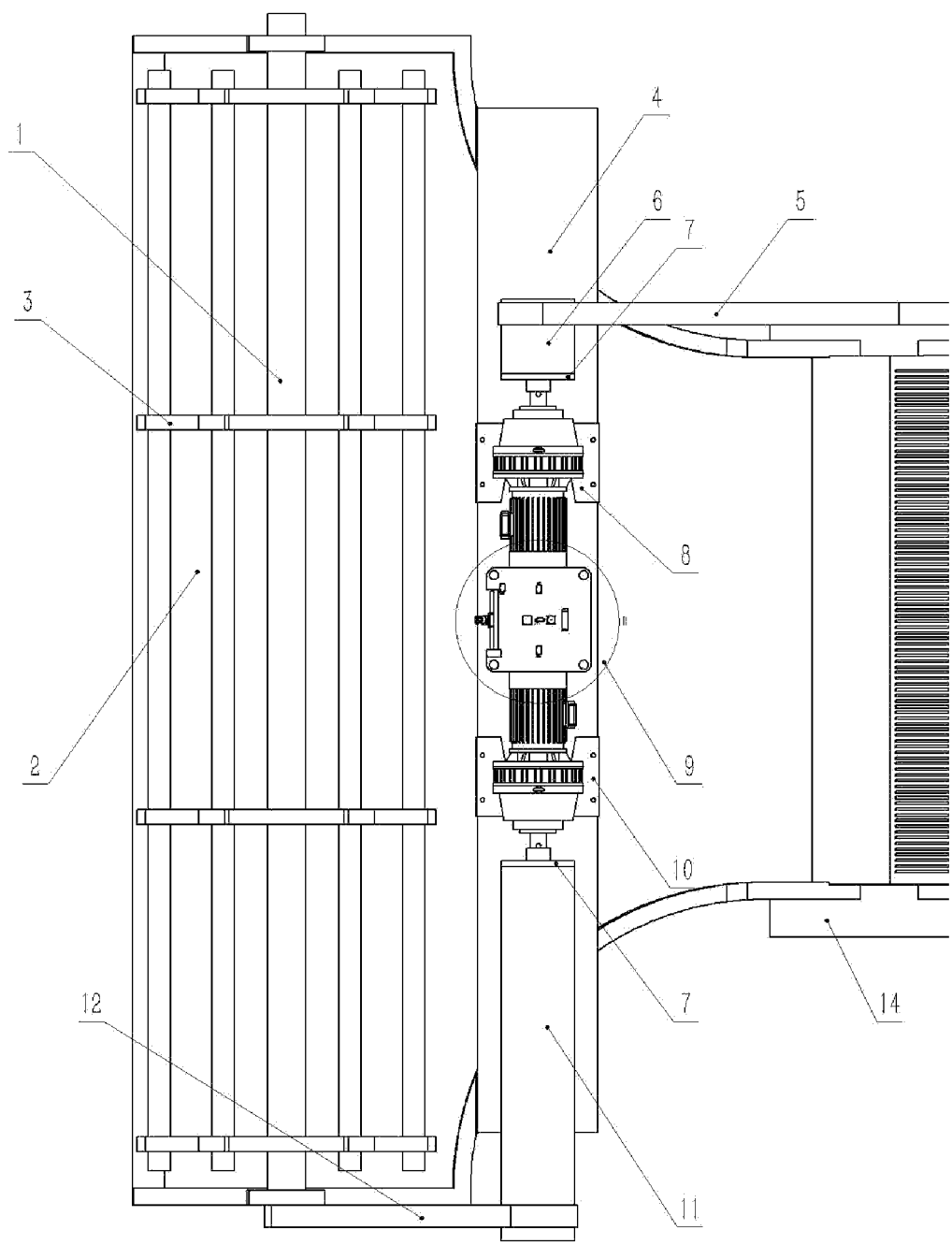
FIG. 1 is a top view of the harvesting part of a header capable of performing lodging detection based on a laser sensor.

Reference numerals: 1. rotating shaft of a roller, 2. harvesting part, 3. roller, 4. motor base plate, 5. transmission belt of the harvesting part, 6. transmission shaft of a motor A, 7. motor arm, 8. high-power motor A, 9. laser sensor control assembly, 10. high-power motor B, 11. transmission shaft of the motor B, 12, transmission belt of the roller, 13. upright lifting column, 14. rotating shaft of the harvesting part, 15. control base plate, 16. battery, 17. power distribution board, 18. voltage reduction module, 19. electronic speed controller, 20. main control board, 21. low-power motor, 22. laser sensor base plate, 23. laser sensor, 24. tube clamp, 25. rotating shaft of the laser sensor, and 26. bearing for stabilizing the rotating shaft of the laser sensor.

DETAILED DESCRIPTION OF THE EMBODIMENTS

The operating process of the harvesting part of a combine harvester capable of performing lodging detection based on a laser sensor is described in detail below with reference to the drawings.

FIG. 1 shows a top view of the harvesting part of a combine harvester capable of performing lodging detection based on a laser sensor. The harvesting part includes a rotating shaft (1) of a roller, a harvesting part (2), rollers (3), a motor base plate (4), a transmission belt (5) of the harvesting part, a transmission shaft (6) of a motor A, motor arms (7), the high-power motor A (8), a laser sensor control assembly (9), a high-power motor B (10), a transmission shaft (11) of the motor B, a transmission belt (12) of the roller, and a rotating shaft (14) of the harvesting part. The motor base plate is fixed to an upper end of the harvesting part; the high-power motor A and the high-power motor B are symmetrically fixed to the motor base plate via positioning holes; the high-power motor A is connected to the transmission shaft of the motor A via a positioning hole in the corresponding motor arm, and the transmission shaft of the motor A transmits torque to the rotating shaft of the harvesting part through the transmission belt of the harvesting part for transmission; and the high-power motor B is connected to the transmission shaft of the motor B via a positioning hole in the corresponding motor arm, and the transmission shaft of the motor B transmits torque to the rotating shaft of the roller through the transmission belt of the roller for transmission, such that the rotating shaft of the roller drives the roller to rotate together.

Figure 2:
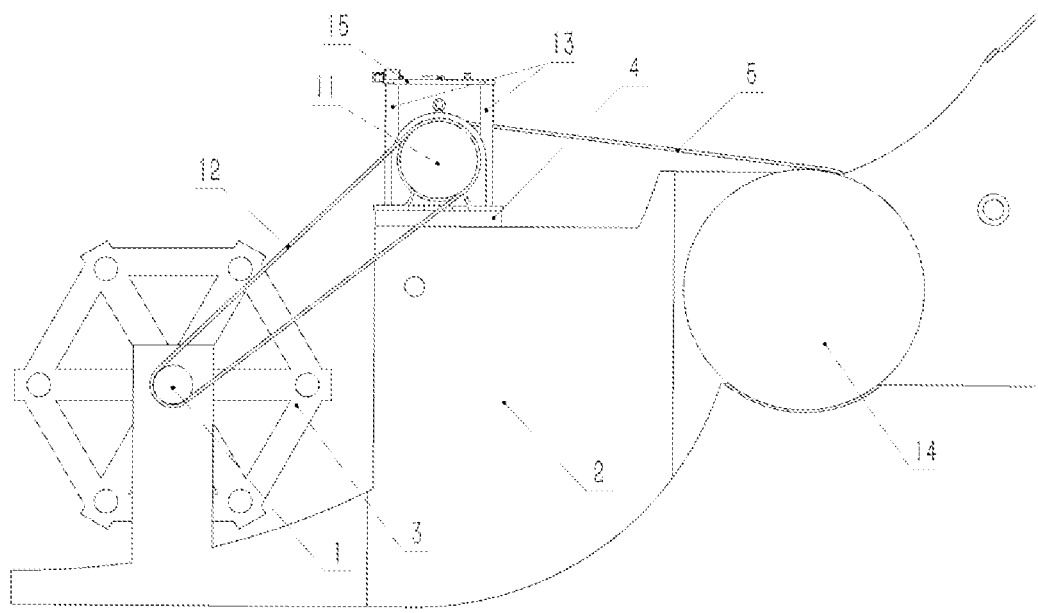
FIG. 2 is a side view of the harvesting part of a header capable of performing lodging detection based on a laser sensor.

FIG. 2 shows a side view of the harvesting part of a combine harvester capable of performing lodging detection based on a laser sensor. The harvesting part includes the rotating shaft (1) of the roller, the harvesting part (2), the roller (3), the motor base plate (4), the transmission belt (5) of the harvesting part, the transmission shaft (11) of the motor B, the transmission belt (12) of the roller, upright lifting columns (13), the rotating shaft (14) of the harvesting part, and a control base plate (15). The transmission shaft of the motor B transmits the torque to the rotating shaft of the roller through the transmission belt of the roller, so as to drive the rollers to move; the transmission shaft of the motor A transmits the torque to the rotating shaft of the harvesting part, so as to control the harvesting part to be lowered or return to be horizontal; the control base plate is fixed above the motor base plate through the upright lifting columns via positioning holes by means of M3 screws.

Figure 3:
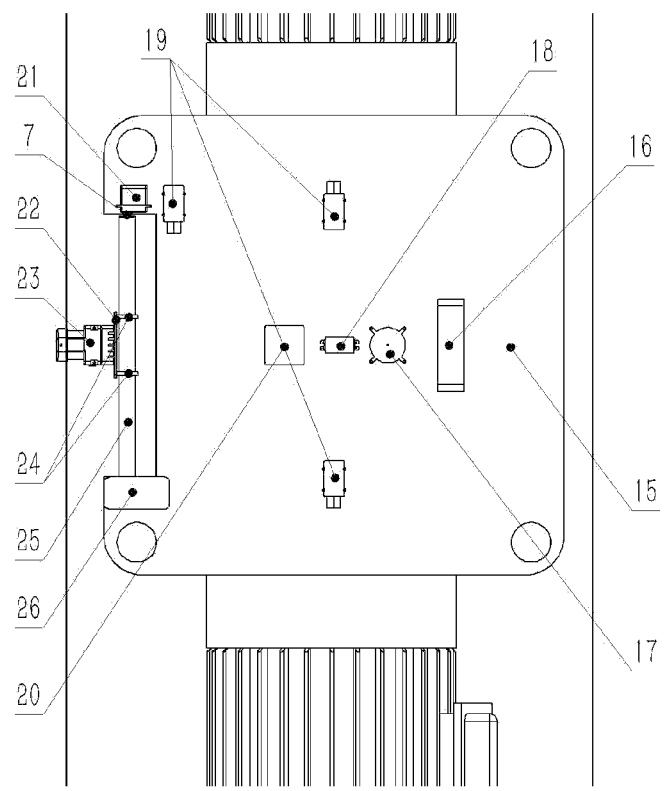
FIG. 3 is a partially enlarged view of a laser sensor control assembly of the harvesting part of a combine harvester capable of performing lodging detection based on a laser sensor.

FIG. 3 shows a partially enlarged view of the laser sensor control assembly of the harvesting part of a combine harvester capable of performing lodging detection based on a laser sensor. The laser sensor control assembly includes the control base plate (15), a battery (16), a power distribution board (17), a voltage reduction module (18), electronic speed controllers (19), a main control board (20), a low-power motor (21), a motor arm (7), a laser sensor base plate (22), a laser sensor (23), tube clamps (24), a rotating shaft (25) of the laser sensor, and a bearing (26) for stabilizing the rotating shaft of the laser sensor. The battery, the power distribution board, the voltage reduction module, the main control board, and three electronic speed controllers are all bonded to the control base plate with double-sided adhesives; the low-power motor is fixed to the control base plate through an L-shaped support and close to a front end of the control base plate; one end of the rotating shaft of the laser sensor is connected to the low-power motor through the motor arm, and the other end of the rotating shaft of the laser sensor is fixed by the bearing for stabilizing the rotating shaft of the laser sensor; and the laser sensor is fixed at the center of the rotating shaft of the laser sensor through the laser sensor base plate by means of the tube clamps. A positive electrode and a negative electrode of the battery are connected to the power distribution board through wires. In this way, power interfaces are increased, and a current is stabilized. The power distribution board leads wires to the three electronic speed controllers; and the electronic speed controller converts a direct current into a three-phase current, and is connected to the corresponding motor through a wire to control the speed of the rotating shaft. the power distribution board also leads a wire to the voltage reduction module and then to a power interface of the main control board; and a pulse-width modulation (PWM) channel of the main control board is connected to a PWM signal wire of the electronic speed controller, so as to achieve a control over the motor.

The present disclosure relates to a control method of an adaptive device for a header capable of performing lodging detection based on a laser sensor. The control method includes the following steps.

Step 1, a main switch of a power supply is turned on to make a low-power motor (21) and a main control board (20) be respectively powered on, where a high-power motor A (8) and a high-power motor B (10) are powered on through an internal diesel generator.

Step 2, when a combine harvester moves forwards, the high-power motor A (8) is controlled by the main control board (20) to adjust a harvesting part to be horizontal, and a basic rotation speed is preset for the high-power motor B (10) through the main control board (20).

Step 3, data preprocessing is performed on a laser sensor (23) through the following steps: firstly, extracting, based on an ROI, data only retained within a threshold range of a preset region in front of the combine harvester; and secondly, filtering outliers in the data by means of a statistical filter.

Step 4, a basic rotation speed is preset for the low-power motor (21) such that the low-power motor (21) drives the laser sensor (23) to repeatedly scan up and down within a constant angle; and a microprocessor receives and stores point cloud data of the laser sensor, and displays the point cloud data within a complete scanning cycle on a serial screen.

Step 5, the microprocessor analyzes and processes the laser point cloud data of N frames, and adjusts an output according to a PID to select different harvesting modes.

The scanning of the laser sensor is mainly fulfilled based on a TOF principle.

The step 4 specifically includes:

The time $t_{laser}$ required for acquiring the data of one frame by the laser sensor is obtained based on a scanning frequency of the laser sensor, and the time $t_{cycle}$ of a complete up-down scanning cycle is calculated according to the basic rotation speed n and magnitude θ of the constant angle of the low-power motor, such that the number N of frames of the laser sensor within the constant angle can be calculated as follows:

$$\omega = 2\pi n \qquad (1)$$

$$t_{cycle} = \frac{\theta}{\omega} \qquad (2)$$

$$N = \text{int}\left(\frac{t_{cycle}}{t_{laser}}\right) \qquad (3)$$

In the formulas, ω represents an angular speed of the low-power motor; int( ) indicates rounding of the number of the frames of the laser sensor; N represents the number of laser frames, calculated according to formula (1), formula (2), and formula (3), within a complete up-down scanning angle; and the microprocessor receives and stores the laser point cloud data of N frames, and displays the laser point cloud data on the serial screen, such that distance information of an object in front of the combine harvester can be visually observed.

The step 5 specifically includes:

The microprocessor receives and stores the laser point cloud data of N frames, and processes the data of N frames, which is taken as being within the complete scanning cycle, through the following steps: firstly, solving a ground fitting equation (4) by means of a least square method to obtain values of parameter a, parameter b, parameter c, and parameter d:

$$ax+by+cy=d \qquad (4)$$

working out a planar thresh $d_i$ of any data point $(x_i, y_i, z_i)$;
setting the planar thresh as Δd, where if $|d_i-d|<\Delta d$, the point is regarded as a ground point; and filtering the ground point; and Secondly, performing DBSCAN on non-ground point cloud data, so as to cluster the data of the object into different clusters by region growing; analyzing features of each cluster according to a clustering result, where the data distribution of crops in a lodging state is obviously different from that of crops in a normal growth state.

An amount of point cloud data of the crops in the lodging state is generally small in a vertical direction; the crops in the lodging state tilt and extend towards a horizontal direction and are intertwined, so that an amount of the point cloud data of the crops in the lodging state is large in the horizontal direction; point cloud data of crops in a normal growth state is evenly distributed in the vertical direction, and an amount of the point cloud data of the crops in the normal growth state is large in the vertical direction; besides, the crops in the normal growth state are uniformly spaced in the horizontal direction, and an obvious jump of the data points in the horizontal direction exists; in this case, the state of the crops can be distinguished according to feature information, based on the clustering result, of the data; if a detection result shows that the crops are in the lodging state, the combine harvester slows down and lowers the harvesting part to guarantee harvesting accuracy, and restores an original speed and enables the harvesting part to return to be horizontal after the crops in a lodging area are completely harvested; and if the detection result shows that the crops are not in the lodging state, the combine harvester continues to move at the original speed and keeps the harvesting part horizontal to guarantee a harvesting speed.

What is claimed is:

1. An adaptive device for a header capable of performing lodging detection based on a laser sensor, comprising a transmission assembly and a laser sensor control assembly, wherein, the transmission assembly comprises a rotating shaft of a roller, a harvesting part, a motor base plate, a transmission belt of the harvesting part, a transmission shaft of a first high-power motor, motor arms, the first high-power motor, a second high-power motor a transmission shaft of the second high-power motor, a transmission belt of the roller, and a rotating shaft of the harvesting part, wherein, the motor base plate is fixed to an upper end of the harvesting part;

the first high-power motor and the second high-power motor are symmetrically fixed to the motor base plate via positioning holes;

the first high-power motor is connected to the transmission shaft of the first high-power motor via a positioning hole in the corresponding motor arm, and the transmission shaft of the first high-power motor transmits torque to the rotating shaft of the harvesting part through the transmission belt of the harvesting part for transmission; and the second high-power motor is connected to the transmission shaft of the second high-power motor via a positioning hole in the corresponding motor arm, and the transmission shaft of the second high-power motor transmits torque to the rotating shaft of the roller through the transmission belt of the roller for transmission; and the laser sensor control assembly comprises the motor base plate, upright lifting columns, a control base plate, a battery, a power distribution board, a voltage reduction module, electronic speed controllers, a main control board, a low-power motor, a laser sensor base plate, a laser sensor, tube clamps, a rotating shaft of the laser sensor, and a bearing for stabilizing the rotating shaft of the laser sensor, wherein, the control base plate is arranged above the motor base plate through the upright lifting columns;

the battery, the power distribution board, the voltage reduction module, the main control board, and three electronic speed controllers are all bonded to the control base plate with double-sided adhesives; the low-power motor is fixed to the control base plate through an L-shaped support and close to a front end of the control base plate;

one end of the rotating shaft of the laser sensor is connected to the low-power motor through the motor arm, and the other end of the rotating shaft of the laser sensor is fixed by the bearing for stabilizing the rotating shaft of the laser sensor; and the laser sensor is fixed at a center of the rotating shaft of the laser sensor through the laser sensor base plate by the tube clamps.

2. The adaptive device for the header capable of performing lodging detection based on the laser sensor according to claim 1, wherein the battery, the power distribution board, the voltage reduction module, the main control board, and the low-power motor are fixed above the control base plate; the first high-power motor and the second high-power motor are symmetrically fixed below the control base plate; a positive electrode and a negative electrode of the battery are connected to the power distribution board through wires; the power distribution board leads the wires to the three electronic speed controllers; the electronic speed controllers convert a direct current into a three-phase current, and are respectively connected to the first high-power motor, the second high-power motor, and the low-power motor through the wires, so as to control rotation of the rotating shaft; the power distribution board also leads a wire to the voltage reduction module and then to a power interface of the main control board; and a pulse-width modulation channel of the main control board is connected to a pulse-width modulation signal wire of the electronic speed controller, so as to achieve a control over the motor.

3. The adaptive device for the header capable of performing lodging detection based on the laser sensor according to claim 2, wherein four power wires are led from the battery; two of the power wires are connected to the power distribution board to shunt a heavy current of the motor; and the other two of the power wires are connected to the voltage reduction module to provide an input voltage for the voltage reduction module.

4. The adaptive device for the header capable of performing lodging detection based on the laser sensor according to claim 2, wherein the voltage reduction module is used to reduce an input voltage and limit the current, an input terminal of the voltage reduction module is connected to the main control board through two 14 awg silicone wires; the power distribution board receives a voltage from a power supply terminal, and four power output wires from the power distribution board are connected to two electronic speed controllers; the electronic speed controller is connected to two power input wires from the power distribution board, and is also connected to one signal input wire and one analog signal ground wire from the main control board; and three output wires from the electronic speed controller is connected to the motor.

5. A control method of an adaptive device for a header capable of performing lodging detection based on a laser sensor, comprising the following steps:

step 1, turning on a main switch of a power supply to make a low-power motor and a main control board be respectively powered on, wherein a first high-power motor and a second high-power motor are powered on through an internal diesel generator;

step 2, when a combine harvester moves forwards, controlling, by the main control board, the first high-power motor to adjust a harvesting part to be horizontal, and presetting, through the main control board, a basic rotation speed for the second high-power motor;

step 3, performing data preprocessing on a laser sensor through the following steps: firstly, extracting, based on a region of interest (ROI), data only retained within a threshold range of a preset region in front of the combine harvester; and secondly, filtering outliers in the data by a statistical filter;

step 4, presetting a basic rotation speed for the low-power motor such that the low-power motor drives the laser sensor to repeatedly scan up and down within a constant angle; and receiving and storing, by a microprocessor, point cloud data of the laser sensor, and displaying, by the microprocessor, the point cloud data within a complete scanning cycle on a serial screen; and step 5, the microprocessor analyzes and processes the laser point cloud data of N frames, and adjusts an output according to a proportion integration differentiation (PID) to select different harvesting modes.

6. The control method of the adaptive device for the header capable of performing lodging detection based on the laser sensor according to claim 5, wherein the scanning of the laser sensor is mainly fulfilled based on a time-of-flight (TOF) principle.

7. The control method of the adaptive device for the header capable of performing lodging detection based on the laser sensor according to claim 5, wherein the step 4 specifically comprises:

obtaining, based on a scanning frequency of the laser sensor, a time $t_{laser}$ required for acquiring the data of one frame by the laser sensor, and calculating a time $t_{cycle}$ of a complete up-down scanning cycle according to the basic rotation speed n and a magnitude θ of the constant angle of the low-power motor, so that the number N of frames of the laser sensor within the constant angle is calculated:

$$\omega = 2\pi n \quad (1)$$

$$t_{cycle} = \frac{\theta}{\omega} \quad (2)$$

$$N = \text{int}\left(\frac{t_{cycle}}{t_{laser}}\right) \quad (3)$$

wherein, ω represents an angular speed of the low-power motor; int( ) indicates rounding of the number of the frames of the laser sensor; N represents the number of laser frames, worked out according to formula (1), formula (2), and formula (3), within a complete up-down scanning angle; and the microprocessor receives and stores the laser point cloud data of N frames, and displays the laser point cloud data on the serial screen, such that distance information of an object in front of the combine harvester is visually observed.

8. The control method of the adaptive device for the header capable of performing lodging detection based on the laser sensor according to claim 5, wherein the step 5 specifically comprises:

receiving and storing, by the microprocessor, the laser point cloud data of N frames, and processing, by the microprocessor, the data of N frames, which is taken as being within the complete scanning cycle, through the following steps: firstly, solving a ground fitting equation by a least square method to obtain values of parameter a, parameter b, parameter c, and parameter d:

$$ax+by+cy=d \quad (4)$$

working out a planar thresh $d_i$ of any data point $(x_i,y_i,z_i)$; setting the planar thresh as Δd, wherein if $|d_i-d|<\Delta d$, the point is regarded as a ground point; and filtering the ground point;

secondly, performing density-based spatial clustering of applications with noise (DBSCAN) on non-ground point cloud data, so as to cluster the data of an object into different clusters by region growing; analyzing features of each cluster according to a clustering result, wherein a data distribution of crops in a lodging state is obviously different from that of crops in a normal growth state:

an amount of point cloud data of the crops in the lodging state is generally small in a vertical direction; the crops in the lodging state tilt and extend towards a horizontal direction and are intertwined, so that the amount of the point cloud data of the crops in the lodging state is large in the horizontal direction; point cloud data of crops in a normal growth state is evenly distributed in the vertical direction, and an amount of the point cloud data of the crops in the normal growth state is large in the vertical direction; besides, the crops in the normal growth state are uniformly spaced in the horizontal direction, and an obvious jump of the data points in the horizontal direction exists; in this case, a state of the crops is distinguished according to feature information, based on the clustering result, of the data; if a detection result shows that the crops are in the lodging state, the combine harvester slows down and lowers the harvesting part to guarantee harvesting accuracy, and restores an original speed and enables the harvesting part to return to be horizontal after the crops in a lodging area are completely harvested; and if the detection result shows that the crops are not in the lodging state, the combine harvester continues to move at the original speed and keeps the harvesting part horizontal to guarantee a harvesting speed.

* * * * *